US011440927B2

(12) United States Patent
Czaplewski-Campbell et al.

(10) Patent No.: US 11,440,927 B2
(45) Date of Patent: Sep. 13, 2022

(54) HYDROXYAPATITE JANUS PARTICLES

(71) Applicant: International Business Machines Corporation, Armonk, NY (US)

(72) Inventors: Sarah Czaplewski-Campbell, Rochester, MN (US); Jason T. Wertz, Pleasant Valley, NY (US); Brandon M. Kobilka, Tucson, AZ (US); Eric Campbell, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 357 days.

(21) Appl. No.: 15/823,838

(22) Filed: Nov. 28, 2017

(65) Prior Publication Data

US 2020/0062788 A1    Feb. 27, 2020

(51) Int. Cl.
*A61K 9/16* (2006.01)
*C07F 9/06* (2006.01)
*C01B 25/32* (2006.01)

(52) U.S. Cl.
CPC .............. *C07F 9/06* (2013.01); *C01B 25/327* (2013.01); *A61L 2430/02* (2013.01)

(58) Field of Classification Search
CPC .......... A61K 9/14; A61K 9/16; A61K 9/1682; A61K 9/1605; A61K 9/1611; A61K 9/1617; A61K 9/1629; A61K 9/1647; A61K 9/1652
See application file for complete search history.

(56) References Cited

U.S. PATENT DOCUMENTS

| | | | |
|---|---|---|---|
| 8,430,053 | B2 | 4/2013 | Taylor et al. |
| 2008/0044830 | A1 | 2/2008 | Tovar et al. |
| 2009/0054619 | A1 | 2/2009 | Baker et al. |
| 2010/0272693 | A1* | 10/2010 | Lee .................... A61L 27/20 424/93.7 |
| 2011/0117171 | A1* | 5/2011 | Melican ............... A61K 47/02 424/426 |
| 2011/0282095 | A1* | 11/2011 | Kjellin ................. A61L 27/50 562/8 |
| 2016/0228550 | A1 | 8/2016 | Karp et al. |
| 2017/0000908 | A1 | 1/2017 | Li et al. |

FOREIGN PATENT DOCUMENTS

CN          106084215 A      11/2016

OTHER PUBLICATIONS

Of Tran et al. (Janus nanoparticles: materials, preparations and recent advances in drug delivery, Expert Opinion, Drug Delivery, Informa UK, 2014, 11(&): 1061-1074) (Year: 2014).*
Balasundaram, et al., "Using hydroxyapatite nanoparticles and decreased crystallinity to promote osteoblast adhesion similar to functionalizing with RGD," Elsevier, Biomaterials, Science Direct, Available online Jan. 23, 2006, 8 pages.
Grignard, et al., "Functionalization of aliphatic polyesters by "click chemistry" in supercritical carbon dioxide," Belgian Polymer Group (BPG) annual meeting 2009, published May 14, 2009, 1 page.
Hankenson, et al., "Extracellular signaling molecules to promote fracture hearing and bone regeneration," Elsevier, Adv Drug Deliv Rev., Nov. 2015, 1 page.
Hong, et al., "Grafting polymerization of L-lactide on the surface of hydroxyapatite nano-crystals," Elsevier, Polymer, Science Direct, Accepted Jul. 20, 2004, 8 pages.
Perro, et al., "Production of large quantities of "Janus" nanoparticles using wax-in-water emulsions," Science Direct, vol. 332, Issue 1, Jan. 5, 2009, 2 pages.
Riva, et al., "Combination of Ring-Opening Polymerization and "Click Chemistry": Toward Functionalization and Grafting of Poly (ε-caprolactone)," ACS Publications, Macromolecules, 2007, 3 pages.
Wright, et al., "Synthesis of Functionalized Poly (lactic acid) Using 2-Bromo-3-hydroxypropionic Acid," ACS Publications, Macromolecules, 2016, 3 pages.
"Azide-alkyne Huisgen cycloaddition," Wikipedia the Free Encyclopedia, Printed Nov. 16, 2017, 5 pages https://en.wikipedia.org/wiki/Azide-alkyne_Huisgen_cycloaddition.
"Carbodiimide," Wikipedia the Free Encyclopedia, Printed Nov. 16, 2017, 2 pages https://en.wikipedia.org/wiki/Carbodiimide.

* cited by examiner

*Primary Examiner* — Micah Paul Young
(74) *Attorney, Agent, or Firm* — Peter J. Edwards (57) ABSTRACT

A hydroxyapatite particle having a plurality of functionalities on a surface, a process for forming a hydroxyapatite particle having a plurality of functionalities on a surface, and an article of manufacture including a hydroxyapatite particle having a plurality of functionalities on a surface are disclosed. The hydroxyapatite particle includes a first functionality on a first surface of the hydroxyapatite particle, where the first functionality includes first moieties to bind to polymer constructs, and a second functionality on a second surface of the hydroxyapatite particle. The process for forming the hydroxyapatite particle includes providing one or more hydroxyapatite particles, forming one or more wax particles, functionalizing a first exposed surface of the one or more hydroxyapatite particles, removing the one or more hydroxyapatite particles from the wax core, and functionalizing the second exposed surface of the one or more hydroxyapatite particles.

10 Claims, 8 Drawing Sheets

Specification includes a Sequence Listing.

SEQUENCE LISTING

```
<160> NUMBER OF SEQ ID NOS: 6

<210> SEQ ID NO 1
<211> LENGTH: 5
<212> TYPE: PRT
<213> ORGANISM: Homo sapiens

<400> SEQUENCE: 1

Tyr Ile Gly Ser Arg

<210> SEQ ID NO 2
<211> LENGTH: 5
<212> TYPE: PRT
<213> ORGANISM: Homo sapiens

<400> SEQUENCE: 2

Ile Lys Val Ala Val

<210> SEQ ID NO 3
<211> LENGTH: 4
<212> TYPE: PRT
<213> ORGANISM: Artificial Sequence
<220> FEATURE:
<223> OTHER INFORMATION: Homo sapiens

<400> SEQUENCE: 3

Arg Glu Asp Val

<210> SEQ ID NO 4
<211> LENGTH: 4
<212> TYPE: PRT
<213> ORGANISM: Artificial Sequence
<220> FEATURE:
<223> OTHER INFORMATION: Synthesized

<400> SEQUENCE: 4

Asp Gly Glu Ala

<210> SEQ ID NO 5
<211> LENGTH: 6
<212> TYPE: PRT
<213> ORGANISM: Artificial Sequence
```

```
<220> FEATURE:
<223> OTHER INFORMATION: Homo sapiens

<400> SEQUENCE: 5

Ser Val Val Tyr Gly Arg

<210> SEQ ID NO 6
<211> LENGTH: 4
<212> TYPE: PRT
<213> ORGANISM: Artificial Sequence
<220> FEATURE:
<223> OTHER INFORMATION: Homo sapiens

<400> SEQUENCE: 6

Val Ala Pro Gly
```

HYDROXYAPATITE JANUS PARTICLES

SEQUENCE LISTING

A text file containing a sequence listing is incorporated by reference herein in its entirety. The name of the text file is AUS820160822US01_ReplacementSequenceListing, the date of creation of the text file is Nov. 14, 2019, and the size of the text file is 791 bytes.

BACKGROUND

The present disclosure relates to hydroxyapatite particles and, more specifically, hydroxyapatite particles with a plurality of functionalities on the surface.

Hydroxyapatite is a calcium phosphate mineral, and a mineral form of calcium apatite, with many uses and applications, especially in relation to bones. Hydroxyapatite has many similarities to bone mineral both in structure and composition, as well as its biocompatibility with human tissue. Hydroxyapatite, thus, has a wide variety of applications such as bone tissue engineering, bone grafts, bone implants and replacements, bone fixation devices, etc.

SUMMARY

Various embodiments are directed toward a hydroxyapatite particle with a plurality of functionalities on a surface. The hydroxyapatite particle may include a first functionality on a first surface of the hydroxyapatite particle, where the first functionality includes first moieties to bind to polymer constructs. The hydroxyapatite particle may also include a second functionality on a second surface of the hydroxyapatite particle, the second surface separate from the first surface. Additional embodiments are directed to a process of forming a hydroxyapatite particle with a plurality of functionalities on a surface. The process may include providing one or more hydroxyapatite particles, forming one or more wax particles, functionalizing a first exposed surface of the one or more hydroxyapatite particles, removing the one or more hydroxyapatite particles from the wax core to expose a second surface of the one or more hydroxyapatite particles, and functionalizing the second exposed surface of the one or more hydroxyapatite particles. Additional embodiments are directed to an article of manufacture including a hydroxyapatite particle with a plurality of functionalities on a surface.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present disclosure relates to hydroxyapatite particles and, more specifically, hydroxyapatite particles with a plurality of functionalities on the surface. While the present disclosure is not necessarily limited to such applications, various aspects of the disclosure may be appreciated through a discussion of various examples using this context.

Hydroxyapatite is widely used in bone tissue engineering, bone grafts, bone fixation devices, etc. due to its similarity to bone mineral both in structure and composition, as well as its biocompatibility with human tissue. Further, hydroxyapatite has been shown to be osteoconductive, meaning it promotes bone growth and regeneration. However, hydroxyapatite on its own has a low mechanical strength and is brittle compared to bone. Additionally, pure hydroxyapatite may not degrade in the human body. Therefore, hydroxyapatite may be incorporated into biodegradable polymer constructs (e.g., polylactic acid, polycaprolactone, poly(lactic-co-glycolic) acid, polyglycolic acid, etc.) that provide biodegradability and flexibility to better meet the biological characteristics and mechanical properties of bone and the human body. However, mixing hydroxyapatite particles and the polymer constructs may result in poor adhesion of the hydroxyapatite particles to the polymer constructs, especially when introduced into the body.

The present disclosure provides a hydroxyapatite particle with a plurality (e.g., two or more) of functionalities on a surface of the hydroxyapatite particle, herein referred to as a hydroxyapatite Janus particle. The hydroxyapatite Janus particle is functionalized on one side with moieties to bind to biodegradable polymer constructs. Functionalizing a first side of the hydroxyapatite Janus particle with moieties to bind to polymer constructs may improve the adhesion of the hydroxyapatite particle to the biodegradable polymer constructs. The hydroxyapatite Janus particle may be functionalized on at least a second side with other moieties. The other moieties may be different than the moieties to bind to biodegradable particles.

In some embodiments, the multiple functionalities may be multiple functional groups. Each of the functionalities may be concentrated on different areas of the surface of the hydroxyapatite particle. In some embodiments, there is some overlap between the different functionalities. In an embodiment, when a hydroxyapatite particle has two functionalities, one functionality may be on half of the hydroxyapatite particle surface and one functionality may be on the other half of the hydroxyapatite particle surface. The hydroxyapatite Janus particles with the plurality of functionalities are further discussed herein and are depicted in FIG. 4.

Figure 1:
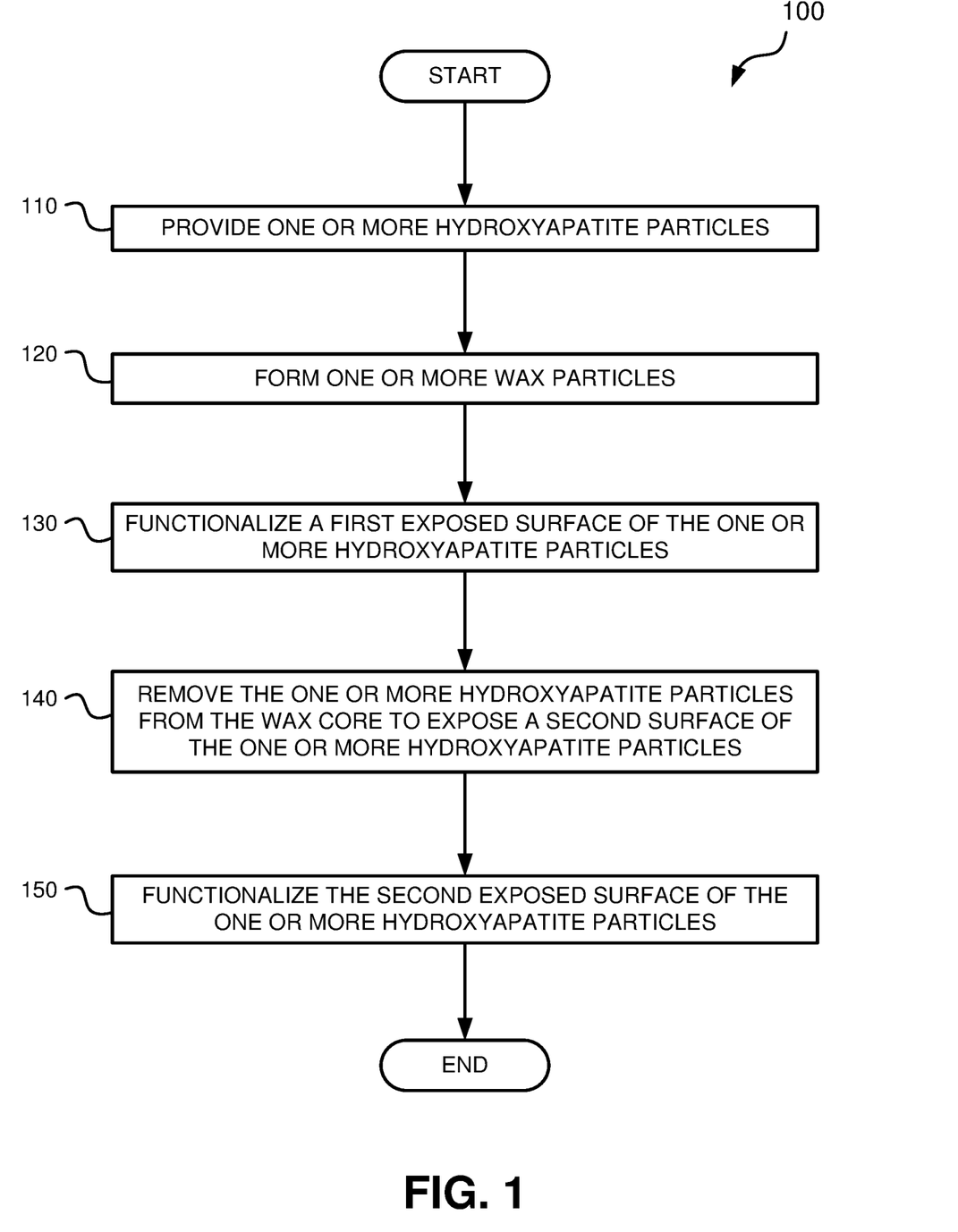
FIG. 1 depicts a flowchart of a set of operations for forming a hydroxyapatite particle with a plurality of functionalities, according to various embodiments.

Referring now to FIG. 1, a flowchart 100 of a set of operations for forming a hydroxyapatite particle with a plurality of functionalities (herein a hydroxyapatite Janus particle) is depicted, according to various embodiments. In some embodiments, a functionality may be a functional group (i.e., moieties that contribute to a compound's properties and reactivity). In an example embodiment, the hydroxyapatite Janus particle is hydroxyapatite Janus particle 400 (FIG. 4).

Figure 4:
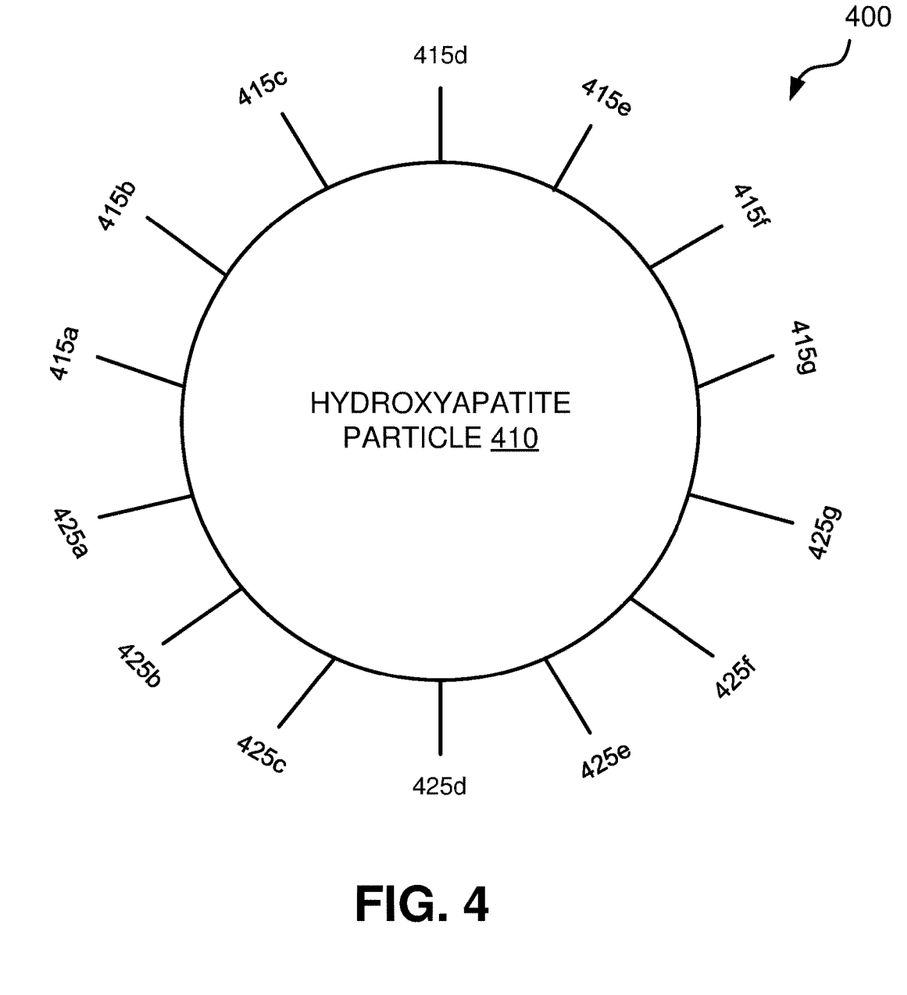
FIG. 4 depicts a schematic diagram of a hydroxyapatite particle with a plurality of functionalities, according to various embodiments.
Figure 5:
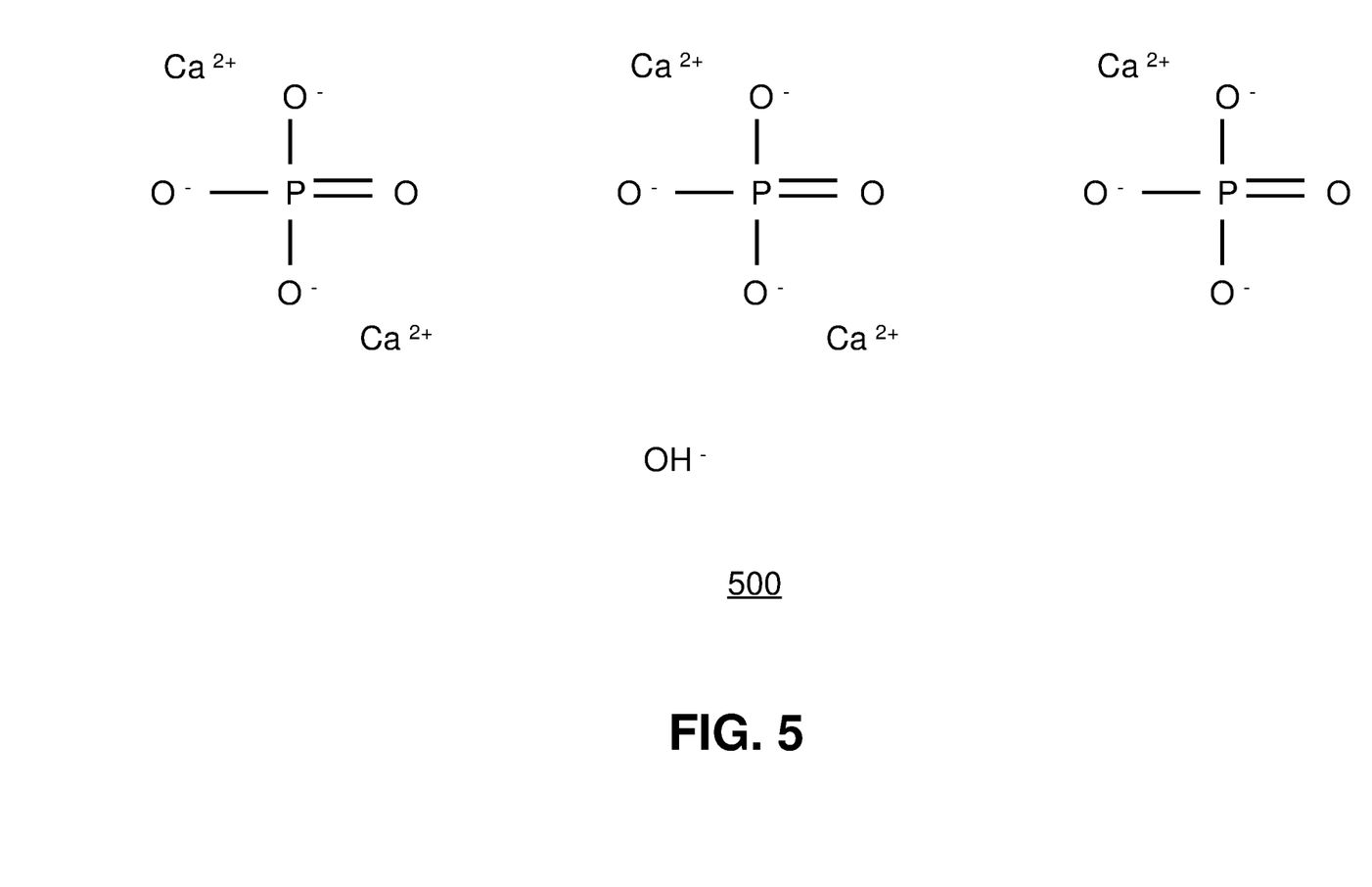
FIG. 5 depicts a diagrammatic representation of a molecular structure of hydroxyapatite, according to various embodiments.

In various embodiments, process 100 begins with operation 110 to provide one or more hydroxyapatite particles, such as hydroxyapatite particle 410 (FIG. 4). Providing the one or more hydroxyapatite particles may include purchasing or producing the hydroxyapatite particles using known methods, in various embodiments. In some embodiments, the hydroxyapatite particles may be microparticles (approximately 0.1 to 100 micrometers in size) and/or nanoparticles (approximately 1 to 100 nanometers in size). Hydroxyapatite has a crystalline structure and is part of the hexagonal crystal system. A hydroxyapatite particle may be crystalline hydroxyapatite. Hydroxyapatite particles are further discussed herein (FIG. 5).

In various embodiments, process 100 continues with operation 120 to form one or more wax particles. The wax particles may include a wax core with the one or more hydroxyapatite particles partially embedded in the wax core. In some embodiments, the wax particle may be wax particle 335 (FIG. 3). Forming the wax particles is further discussed herein and depicted in FIG. 2.

In various embodiments, process 100 continues with operation 130 to functionalize a first exposed surface of the one or more hydroxyapatite particles. Functionalizing the exposed surface yields a partially functionalized hydroxyapatite particle, where a partially functionalized hydroxyapatite particle is a particle with a functionalized portion (e.g., half) of its surface. In various embodiments, the exposed surface of the hydroxyapatite particle is half of the particle surface. In some embodiments, functionalizing a particle includes adding functional groups to the particle. Functionalizing the exposed surface of the one or more hydroxyapatite particles may include introducing (e.g., reacting) first moieties, the first moieties being functional groups, to the exposed surface. The first moieties functionalize the exposed surface of the one or more hydroxyapatite particles to bind to polymer constructs. The first moieties may be either azide groups or alkyne groups.

Hydroxyapatite naturally has hydroxyl groups on its surface. In some embodiments, functionalizing the first exposed surface includes introducing, or reacting, first moieties that will react with the hydroxyl groups to form either azide groups or alkyne groups. These first moieties may include azide groups or alkyne groups.

In some embodiments, functionalizing a first exposed surface of the one or more hydroxyapatite particles includes functionalizing the exposed surface of the hydroxyapatite particles with the first moieties to bind to polymer constructs and then reacting the first moieties with a functionalized polymer construct, yielding the first exposed surface bound to the polymer construct. In an embodiment, when the first moieties are alkyne groups, the alkyne groups may be bound to, or reacted with, azide-functionalized polymer constructs. The alkyne groups may be reacted with azide-functionalized polymer constructs using click chemistry, discussed further herein. In other embodiments, when the first moieties are azide groups, the azide groups may be bound to, or reacted with, alkyne-functionalized polymer constructs. The azide groups may be reacted with the alkyne-functionalized polymer constructs using direct surface functionalization, indirect functionalization using ethanolic linkers, or any other method known in the art. Reacting the first moieties with the functionalized polymer construct is further discussed herein and depicted in FIG. 6, FIG. 7, and FIG. 8. Reaction 600 (FIG. 6), reaction 700 (FIG. 7), and reaction 800 (FIG. 8) are three possible reactions for functionalizing a first exposed surface of the one or more hydroxyapatite particles. Functionalizing the first exposed surface of the one or more hydroxyapatite particles can be done using any known mechanisms.

In various embodiments, process 100 continues with operation 140 to remove the one or more hydroxyapatite particles from the wax core to expose a second surface of the one or more hydroxyapatite particles. After the functionalization of the first exposed surface (operation 130), the hydroxyapatite particles may be removed from their wax confines (the wax core) to yield a partially functionalized hydroxyapatite particle. In an embodiment, the first exposed surface is approximately half of the hydroxyapatite particle surface and the second exposed surface is the other half of the hydroxyapatite particle surface. In some embodiments, a hydrocarbon solvent is used to dissolve the wax, freeing the hydroxyapatite particle from the wax core. Examples of hydrocarbon solvents may include benzene, hexane, heptane, kerosene, pentane, petroleum, toluene, xylene, or any other hydrocarbon solvents known to dissolve wax. Once the hydroxyapatite particles are separated from the wax, the hydroxyapatite particles may be repeatedly washed and separated until no wax remains on the hydroxyapatite particle. Washing and separating the particles may include centrifuging and decanting the hydroxyapatite particles. The resulting hydroxyapatite particle may be a partially functionalized hydroxyapatite particle with a portion of the surface functionalized, and a second portion of the surface exposed, but not yet functionalized.

In various embodiments, process 100 continues with operation 150 to functionalize the second exposed surface of the one or more hydroxyapatite particles. In some embodiments, the second exposed surface may be the surface previously embedded in the wax core. Functionalizing the second exposed surface yields a hydroxyapatite Janus particle, where a hydroxyapatite Janus particle is a particle with a plurality of functionalities on its surface. The hydroxyapatite particles may be functionalized with second moieties. In various embodiments, functionalizing the second exposed surface includes adding second functional groups (e.g., second moieties) to the particle. The second moieties, different from the first moieties, may be reacted with the exposed surface of the hydroxyapatite particle.

In some embodiments, the second moieties are bioactive molecules. These bioactive molecules may promote bone growth, bone development, bone regeneration, bone differentiation, cell adhesion, cell growth, cell proliferation, cell differentiation, or any other functions. In various embodiments, bioactive molecules may include growth factors, growth factor binding domains derived from other proteins, peptide sequences, proteins, antibodies, cytokines, drugs, deoxyribonucleic acid (DNA), and ribonucleic acid (RNA). Examples of bioactive molecules may include RGD peptides, YIGSR peptides (SEQ ID NO: 1), IKVAV peptides (SEQ ID NO: 2), fibronectin-derived REDV peptides (SEQ ID NO: 3), collagen I mimetic DGEA peptides (SEQ ID NO: 4), osteopontin-derived SVVYGR peptides (SEQ ID NO: 5), elastin-derived VAPG peptides (SEQ ID NO: 6), a peptido-mimetic, galactose, lactose, vascular endothelial growth factor, fibronectin domain III 12-14, EC2 cells, bone morphogenetic protein 2 (BMP2), bone morphogenetic protein 7 (BMP7), calcium phosphate, dexamethasone, glycerolphosphate, transforming growth factor beta (TGF-beta), basic fibroblast growth factor, SH3 domain-containing proteins, SH3-binding peptides, nerve growth factor, etc. Bioactive molecules such as the RGD, YIGSR (SEQ ID NO: 1), and/or IKVAV (SEQ ID NO: 2) peptides may promote cell adhesion. Bioactive molecules such as BMP2, BMP7, dexamethasone, glycerolphosphate, TGF-beta may promote bone growth, healing, and/or differentiation. In some embodiments, the bioactive molecules may bind with the existing hydroxyl groups on the surface of the hydroxyapatite particle. In other embodiments, a functional group may be added to the surface of the hydroxyapatite particle (e.g., by reacting the functional group with the hydroxyl group) to bind with the bioactive molecules.

Functionalizing the second exposed surface of the hydroxyapatite particles may be done using known methods to react the second moieties to the surface of the hydroxyapatite particles. In an example reaction, the exposed surface of the hydroxyapatite particle may be reacted with an aminofunctional organosilane (e.g., 3-aminopropyltriethoxysilane (APTES)) and hexane to form an amine compound attached to the hydroxyapatite particle. The amine compound may be reacted with a solvent (such as N,N-dimethylformamide (DMF)) and a cross-linker (such as N-succinimidyl-3-maleimido propionate (SMP)) in order to substitute the terminal amine of the amine compound with the cross-linker. The cross-linker substituted compound may then be reacted with a solvent (such as DMF) and a peptide, the peptide being the bioactive molecule, in order to functionalize the second exposed surface of the hydroxyapatite particle with a bioactive molecule, thus forming a hydroxyapatite Janus particle.

In another example, the amine compound discussed herein may be reacted with N,N'-dicyclohexylcarbodiimide (DCC) and a peptide, the peptide being the bioactive molecule, to bind the amine directly to the peptide, thus functionalizing the second exposed surface of the hydroxyapatite particle with a bioactive molecule and forming a hydroxyapatite Janus particle. In the example reactions discussed herein, the peptide molecules may be replaced with a protein, the protein being the bioactive molecule. Other surface modifications and linkers could also be used to bind the biomolecules.

In various embodiments, the process described herein may be used to functionalize additional surfaces of the one or more hydroxyapatite particles. For example, two-thirds of the hydroxyapatite particle may be embedded in the wax particle, and one-third of the particle may become functionalized with first moieties. Once the portion of the hydroxyapatite particle is functionalized, the partially functionalized hydroxyapatite particle may be partially removed from the wax core (e.g., one-third of the hydroxyapatite particle embedded in the wax core, one-third of the hydroxyapatite particle newly exposed, and one-third of the hydroxyapatite particle functionalized). The newly exposed portion of the hydroxyapatite particle may then be functionalized with second moieties different from the first moieties. Once the second portion of the hydroxyapatite particle is functionalized, the hydroxyapatite particle may be completely removed from the wax core, thus exposing a third surface of the hydroxyapatite particle. The third surface of the hydroxyapatite particle may then be functionalized with third moieties, resulting in a hydroxyapatite Janus particle with three functionalities. A similar process may be used for any number of functionalities.

Figure 2:
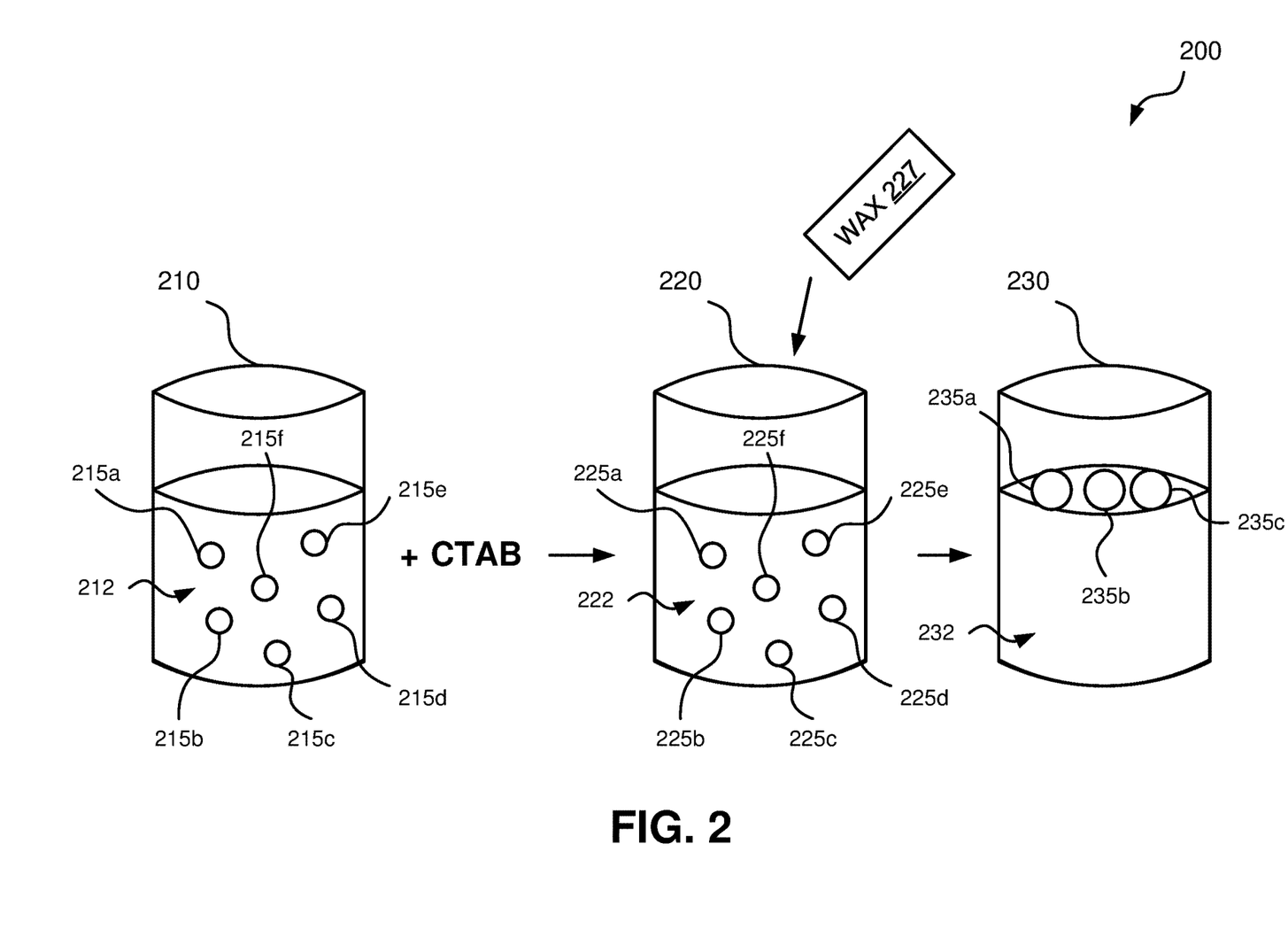
FIG. 2 depicts a schematic diagram of the formation of wax particles, according to various embodiments.
Figure 3:
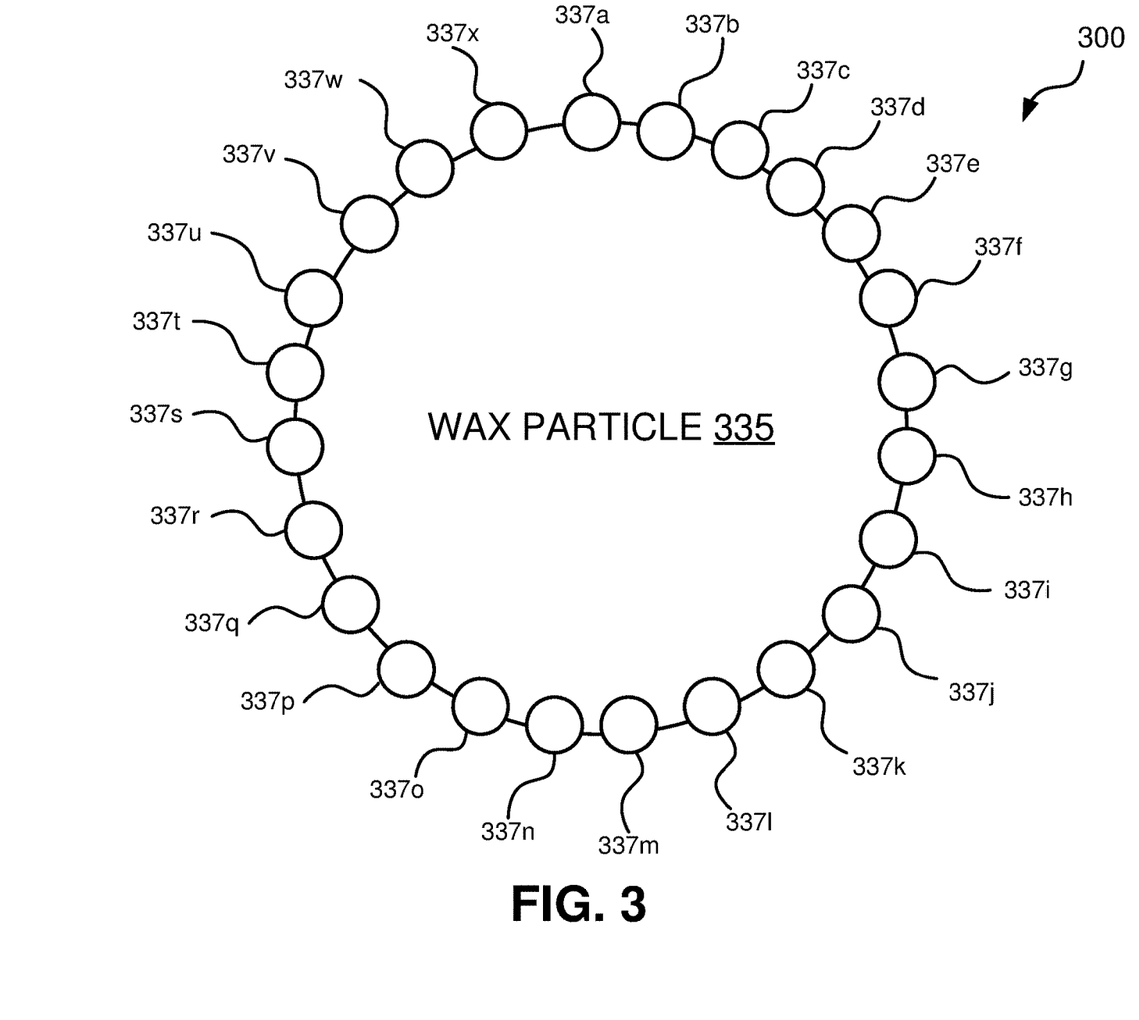
FIG. 3 depicts a schematic diagram of a wax particle, according to various embodiments.

Referring to FIG. 2, a schematic diagram illustrating a sample process 200 of forming wax particles 235a-235c is depicted, according to various embodiments. Process 200 is one possible reaction for forming wax particles 235a-235c, and is provided for illustrative purposes. FIG. 2 is a schematic diagram and is not drawn to scale. Additionally, the schematic diagram depicts a limited number of hydroxyapatite particles and wax particles for illustrative purposes. Process 200 may include any number of hydroxyapatite particles and any number of wax particles.

In various embodiments, forming a wax particle 235a-235c may include forming an aqueous mixture 210 containing the one or more hydroxyapatite particles 215a-215f. In some embodiments, forming the aqueous mixture 210 includes dispersing hydroxyapatite particles 215a-215f in an aqueous solution 212 (e.g., ethanol/water solution) and then mixing. The hydroxyapatite particles 215a-215f may be dispersed into the aqueous solution 212 at an elevated temperature, in some embodiments, which allows for wax to melt when added to the mixture 210 (discussed herein). The aqueous mixture 210 may be a suspension, where the hydroxyapatite particles 215a-215f are suspended through the aqueous solution 212, as depicted in FIG. 2.

In various embodiments, forming wax particles 235a-235c further includes partially hydrophobizing a surface of the one or more hydroxyapatite particles 215a-215f. Hydrophobizing the surface of the hydroxyapatite particles 215a-215f refers to increasing the hydrophobicity of the surface (e.g., the extent to which it repels or does not mix with water). Partially hydrophobizing the surface of the hydroxyapatite particles 215a-215f may include making one portion of the surface (e.g., one half) hydrophobic. In some embodiments, cetyltrimethylammonium bromide (CTAB) is added to the aqueous mixture 210 to partially hydrophobize the surface of the hydroxyapatite particles 215a-215f. A low concentration of CTAB may be used, to avoid a formation of a bilayer, or a film, at the surface of the hydroxyapatite particle 215a-215f. Other surfactants may be used in place of CTAB. Example surfactants may include: cetylpyridinium chloride, benzalkonium chloride, benzethonium chloride, dimethyldioctadecylammonium chloride, dioctadecyldimethylammonium bromide, etc. Aqueous mixture 220 includes partially hydrophobized hydroxyapatite particles 225a-225f and aqueous solution 222.

In various embodiments, forming the wax particles 235a-235c further includes adding wax 227 (e.g., paraffin wax, fluorinated wax, etc.) to the aqueous mixture 220. The wax 227 may be added at an elevated temperature so that the wax 227 is in liquid form. In various embodiments, the wax 227 is added, or deposited, on top of the hydroxyapatite particle suspension in aqueous mixture 220. The solution 220, including the wax 227, may then be vigorously stirred at an elevated temperature. Stirring the solution at the elevated temperature may result in an adsorption at the aqueous solution (e.g., oil/water) interface, and may cause the hydrophobic portion, or side, of the hydroxyapatite particles 225a-225f to adhere to the wax 227. Aqueous mixture 230 includes wax particles 235a-235c and aqueous solution 232. FIG. 3 depicts an example wax particle 335.

In various embodiments, forming the wax particles 235a-235c further includes cooling the aqueous mixture 230 to solidify the wax particles 235a-235c. After cooling (e.g., to room temperature), the wax 227 dissolved in the aqueous mixture 220 solidifies into solid droplets with the hydroxyapatite particles 225a-225f partially extruding from the surface. These wax droplets with the partially exposed hydroxyapatite particles 225a-225f are referred to herein as wax particles 235a-235c. FIG. 2 depicts wax particles 235a-235c at a surface of the aqueous solution 232. In various embodiments, wax particles 235a-235c may be substantially the same as wax particle 335 (FIG. 3).

In some embodiments, after the wax particles 235a-235c are formed, the wax particles 235a-235c are washed with an acid to remove the CTAB (or another surfactant) and expose the hydroxyapatite particle surface.

Referring to FIG. 3, a schematic diagram 300 of a wax particle 335 is depicted, according to various embodiments. In some embodiments, wax particle 335 may be formed after an adsorption reaction, such as the reaction depicted in FIG. 2. Wax particle 335 may include hydroxyapatite particles 337a-337x partially embedded in the wax surface. There may be one or more hydroxyapatite particles embedded in the wax. In various embodiments, wax particle 335 is a colloidosome, with a wax core and hydroxyapatite particles 337a-337x as colloid particles that make up the shell of the wax particle 335.

Referring to FIG. 4, a schematic diagram of a hydroxyapatite Janus particle 400 with a plurality of functionalities is depicted, according to various embodiments. The hydroxyapatite Janus particle 400 may include a hydroxyapatite particle 410 at its core. In some embodiments, hydroxyapatite particle 410 may be a crystalline hydroxyapatite microparticle or nanoparticle.

Hydroxyapatite Janus particle 400 may include a first functionality on a first surface (e.g., half of the surface) of the hydroxyapatite particle 410. The first functionality may include first moieties 415a-415g. In various embodiments, first moieties 415a-415g are moieties to bind to polymer constructs (e.g., azide groups or alkyne groups). Hydroxyapatite Janus particle 400 may further include a second functionality on a second surface (e.g., the other half of the surface) of the hydroxyapatite particle 410. The second functionality may include second moieties 425a-425g. In some embodiments, first moieties 415a-415g are different than second moieties 425a-425g. The second surface may be separate, but may have slight overlap, with the first surface. In various embodiments, second moieties 425a-425g may be bioactive molecules.

In various embodiments, first moieties 415a-415g are azide groups. When first moieties 415a-415g are azide groups, the polymer constructs may be alkyne-functionalized polymer constructs, the polymer constructs functionalized with alkyne groups. The alkyne groups of the polymer constructs may react, or bind, with the azide groups of the hydroxyapatite Janus particle 400, thus binding the hydroxyapatite particle 410 with the polymer constructs. Example polymer constructs may include polylactic acid (PLA), polycaprolactone (PCL), polyglycolic acid (PGA), and poly (lactic-co-glycolic) acid (PLGA).

In various embodiments, first moieties 415a-415g are alkyne groups. When first moieties 415a-415g are alkyne groups, the polymer constructs may be azide-functionalized polymer constructs, the polymer constructs functionalized with azide groups. The azide groups of the polymer constructs may react, or bind, with the alkyne groups of the hydroxyapatite Janus particle 400, thus binding the hydroxyapatite particle 410 with the polymer constructs.

In various embodiments, a hydroxyapatite particle with a plurality of functionalities on a surface of the hydroxyapatite particle, such as hydroxyapatite Janus particle 400, is included in an article of manufacture. In some embodiments, the article of manufacture includes a material that contains the hydroxyapatite Janus particle. The material can be a resin, plastic, adhesive, or polymer. Examples of polymer materials can include polyurethane, epoxies, polyhydroxyurethane, polycarbonates, polyester, polyacrylates, polyimides, polyamides, polyureas, poly(vinyl-ester), etc. The article of manufacture may further include an electronic component.

Referring to FIG. 5, a diagrammatic representation of a molecular structure of hydroxyapatite 500 is depicted, according to various embodiments. The formula of hydroxyapatite is $Ca_5(PO_4)_3OH$. Hydroxyapatite structure 500 depicts a single hydroxyapatite entity with five calcium atoms, three phosphate molecules, and one hydroxide molecule, as suggested by the hydroxyapatite formula. As discussed herein, hydroxyapatite has a crystalline structure and is part of the hexagonal crystal system. A crystal unit cell of hydroxyapatite includes two hydroxyapatite entities. Hydroxyapatite particles, such as hydroxyapatite particle 410, are crystalline hydroxyapatite particles and may include any number of crystal unit cells.

Figure 6:
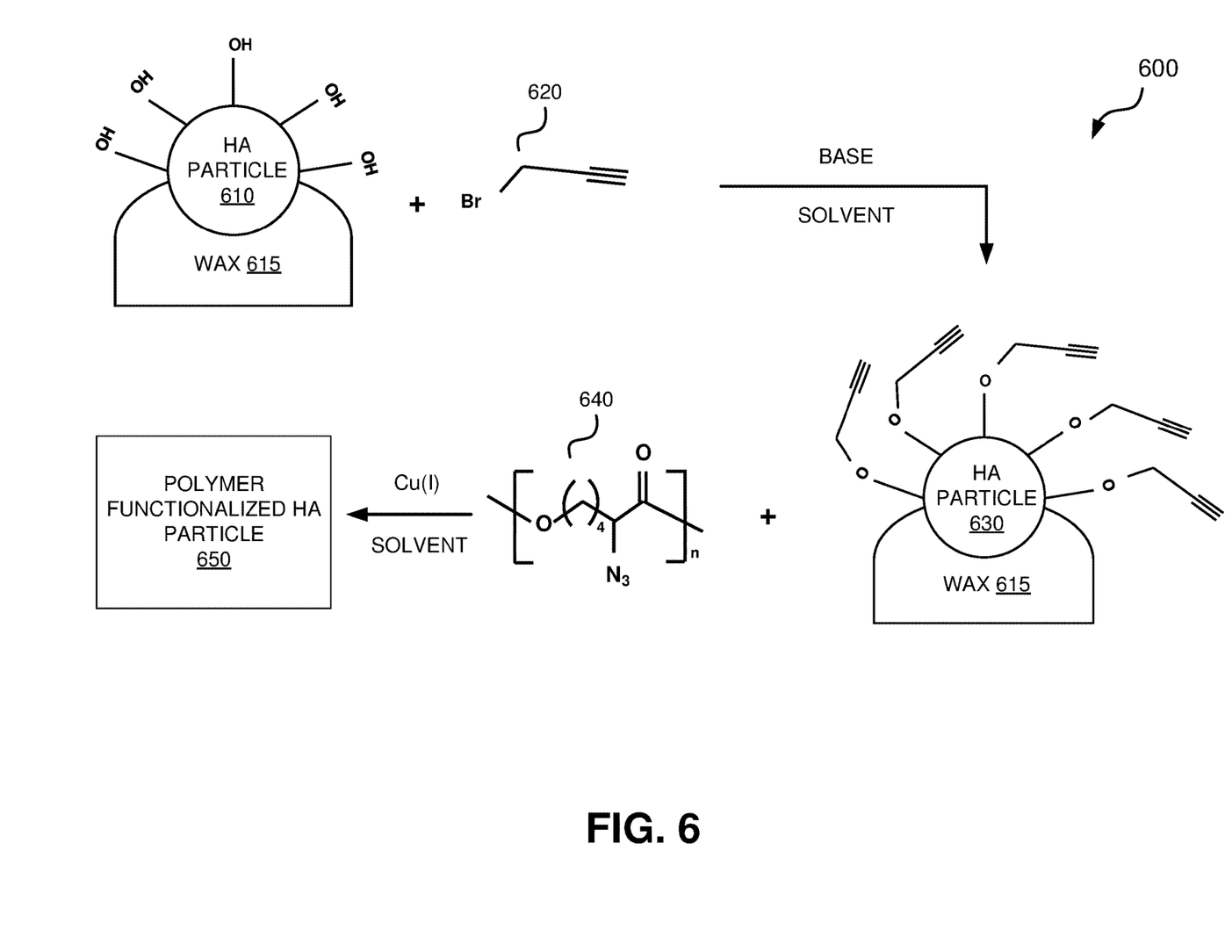
FIG. 6 depicts a first chemical reaction diagram illustrating a process of functionalizing a surface of a hydroxyapatite particle, according to various embodiments.

Referring to FIG. 6, a chemical reaction diagram illustrating a sample process 600 of functionalizing a surface of a hydroxyapatite particle is depicted, according to various embodiments. Functionalizing the surface of the hydroxyapatite particle may include functionalizing a hydroxyapatite particle with first moieties to bind to polymer constructs and then reacting the first moieties with a functionalized polymer construct, yielding the first exposed surface bound to the polymer construct. Process 600 is only one possible reaction for functionalizing a surface of a hydroxyapatite particle, and is illustrated for example purposes.

Process 600 depicts a click chemistry reaction for binding an alkyne-functionalized hydroxyapatite particle with an azide-functionalized polymer construct. In various embodiments, process 600 is a Huisgen 1,3-dipolar cycloaddition click chemistry reaction. Process 600 may begin with a hydroxyapatite (HA) particle 610 partially embedded in wax 615. The hydroxyapatite particle 610 includes hydroxyl groups on its surface. In various embodiments, hydroxyapatite particle 610 and wax 615 are part of a wax particle, such as wax particle 335 (FIG. 3).

Process 600 may continue by reacting 3-bromopropyne 620 with the exposed surface of hydroxyapatite particle 610. 3-bromopropyne 620 is an example alkyne molecule and could be replaced by any alkyne molecule (i.e., a molecule with an alkyne functional group). In process 600, 3-bromopropyne 620 is the first moiety to bind to polymer constructs. A base (e.g., N,N-diisopropylethylamine, triethylamine, etc.) and a solvent may also be added to the reaction. Reacting 3-bromopropyne 620 with the hydroxyapatite particle 610 may functionalize the hydroxyapatite particle 610, resulting in functionalized hydroxyapatite (HA) particle 630 with an alkyne-functionalized exposed surface. In various embodiments, the hydroxyapatite particle surface that is embedded in the wax is not functionalized by 3-bromopropyne 620.

Process 600 may continue by reacting functionalized hydroxyapatite particle 630 with a functionalized polymer construct, in order to bind the hydroxyapatite particle 630 with the polymer construct. Because hydroxyapatite particle 630 is functionalized with alkyne functional groups, the functionalized polymer construct is an azide-functionalized polymer construct. In process 600, the azide-functionalized polymer construct is azide-functionalized PCL 640.

Reacting functionalized hydroxyapatite particle 630 with azide-functionalized PCL 640 may be a copper catalyzed click chemistry reaction, with copper (I) and a solvent included in the reaction. In some embodiments, copper (I) may be a commercial source of copper (I) (e.g., iodide, bromide, etc.). In other embodiments, copper (I) is produced using a reducing agent and copper (II). Example solvents used in process 600 may include alcohols, dimethyl sulfoxide, DMF, tert-butyl alcohol, acetone, tetrahydrofuran, acetonitrile, toluene, etc. In some embodiments, as depicted, hydroxyapatite particle 630 is still embedded in wax 615 when hydroxyapatite particle 630 is reacted with, or bound to, azide-functionalized PCL 640. In other embodiments, wax 615 is separated, or removed, from hydroxyapatite particle 630 before reacting the hydroxyapatite particle 630 with the azide-functionalized PCL 640. Reacting functionalized hydroxyapatite particle 630 with azide-functionalized PCL 640 may result in polymer-functionalized hydroxyapatite particle 650. Polymer-functionalized hydroxyapatite particle 650 includes a hydroxyapatite particle bound to a polymer construct, specifically a molecule containing PCL.

Figure 7:
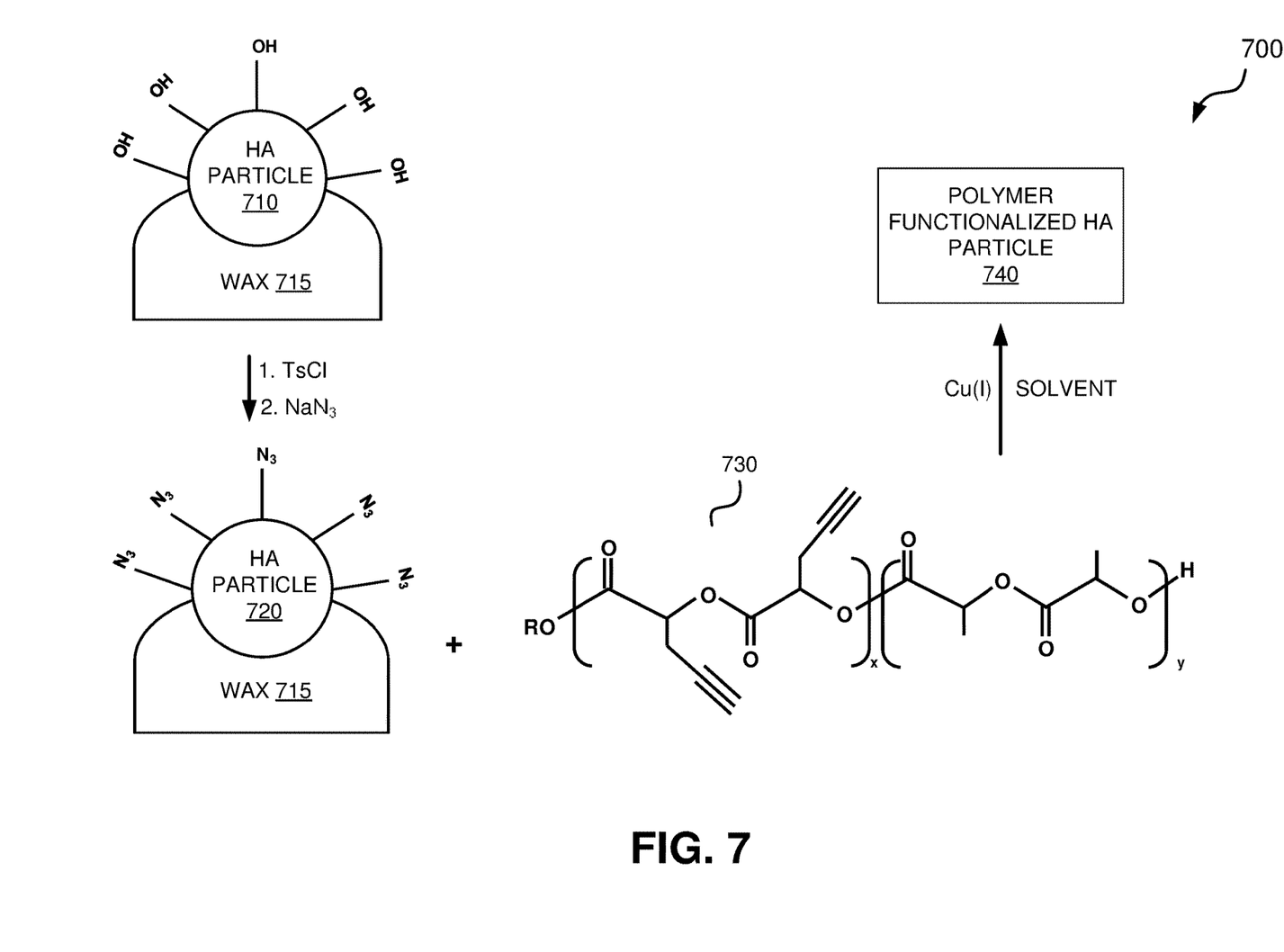
FIG. 7 depicts a second chemical reaction diagram illustrating a process of functionalizing a surface of a hydroxyapatite particle, according to various embodiments.

Referring to FIG. 7, a chemical reaction diagram illustrating a sample process 700 of functionalizing a surface of a hydroxyapatite particle is depicted, according to various embodiments. Functionalizing the surface of the hydroxyapatite particle may include functionalizing a hydroxyapatite particle with first moieties to bind to polymer constructs and then reacting the first moieties with a functionalized polymer construct. Process 700 is only one possible reaction for functionalizing a surface of a hydroxyapatite particle, and is illustrated for example purposes.

Process 700 depicts a reaction for binding an azide-functionalized hydroxyapatite particle with an alkyne-functionalized polymer construct. In various embodiments, process 700 is a Huisgen 1,3-dipolar cycloaddition click chemistry reaction. Process 700 may begin with a hydroxyapatite (HA) particle 710 embedded in wax 715. The hydroxyapatite particle 710 includes hydroxyl groups on its surface. In various embodiments, hydroxyapatite particle 710 and wax 715 are part of a wax particle, such as wax particle 335 (FIG. 3).

Process 700 may continue by reacting hydroxyapatite particle 710 with a reagent, such as 4-toluenesulfonyl chloride (TsCl), and an azide molecule, such as sodium azide (NaN$_3$). Sodium azide is an example azide molecule and could be replaced by any azide molecule (i.e., a molecule with an azide functional group). In process 700, sodium azide is the first moiety to bind to polymer constructs. Reacting sodium azide with the hydroxyapatite particle 710 may functionalize the hydroxyapatite particle 710, resulting in functionalized hydroxyapatite (HA) particle 720 with an azide-functionalized exposed surface. In various embodiments, the azide particle surface that is embedded in the wax is not functionalized by sodium azide.

Process 700 may continue by reacting hydroxyapatite particle 720, with an azide functionalized exposed surface, with a functionalized polymer construct, in order to bind the hydroxyapatite particle 720 with the polymer construct. Because hydroxyapatite particle 720 is functionalized with azide functional groups, the functionalized polymer construct is an alkyne-functionalized polymer construct. In process 700, the alkyne-functionalized polymer construct is an alkyne-functionalized PLA 730.

Reacting hydroxyapatite particle 720 with alkyne-functionalized PLA 730 may be a copper catalyzed click chemistry reaction, with copper (I) and a solvent included in the reaction. In some embodiments, as depicted, hydroxyapatite particle 720 is still embedded in wax 715 when hydroxyapatite particle 720 is reacted with, or bound to, alkyne-functionalized PLA 730. In other embodiments, wax 715 is separated, or removed, from hydroxyapatite particle 720 before reacting the hydroxyapatite particle with the alkyne-functionalized PLA 730. Reacting hydroxyapatite particle 720 with alkyne-functionalized PLA 730 may result in polymer-functionalized hydroxyapatite particle 740. Polymer-functionalized hydroxyapatite particle 740 includes a hydroxyapatite particle bound to a polymer construct, specifically a molecule containing PLA. The hydroxyapatite particle 710 may be bound to alkyne-functionalized PLA 730 using any known mechanisms. For example, the hydroxyl groups on the surface of the hydroxyapatite particle 710 may ring open lactide monomers, grafting PLA from the surface.

Figure 8:
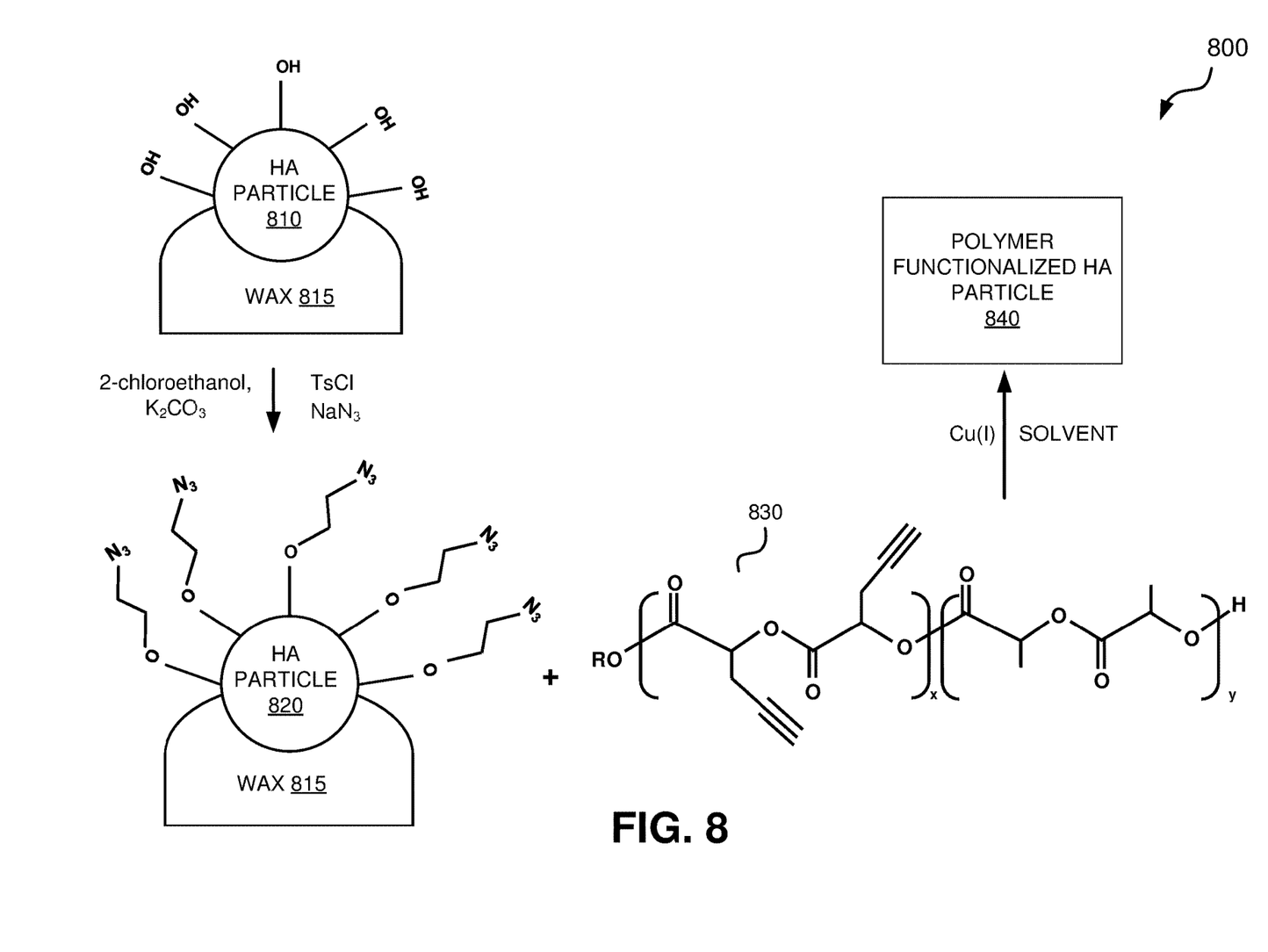
FIG. 8 depicts a third chemical reaction diagram illustrating a process of functionalizing a surface of a hydroxyapatite particle, according to various embodiments.

Referring to FIG. 8, a chemical reaction diagram illustrating a sample process 800 of functionalizing a surface of a hydroxyapatite particle is depicted, according to various embodiments. Functionalizing the surface of the hydroxyapatite particle may include functionalizing a hydroxyapatite particle with first moieties to bind to polymer constructs and then reacting the first moieties with a functionalized polymer construct. Process 800 is only one possible reaction for functionalizing a surface of a hydroxyapatite particle, and is illustrated for example purposes.

Process 800 depicts a reaction for binding an azide-functionalized hydroxyapatite particle with an alkyne-functionalized polymer construct. In various embodiments, process 800 is a Huisgen 1,3-dipolar cycloaddition click chemistry reaction. Process 800 may begin with a hydroxyapatite (HA) particle 810 embedded in wax 815. The hydroxyapatite particle 810 includes hydroxyl groups on its surface. In various embodiments, hydroxyapatite particle 810 and wax 815 are part of a wax particle, such as wax particle 335 (FIG. 3).

Process 800 may continue by indirectly functionalizing hydroxyapatite particle 810 using ethanolic linkers. Hydroxyapatite particle 810 may be reacted with 2-chloroethanol and potassium carbonate ($K_2CO_3$) as well as a reagent, such as 4-toluenesulfonyl chloride (TsCl), and an azide molecule, such as sodium azide (NaN$_3$). The 2-chloroethanol and potassium carbonate may link the azide molecule to hydroxyapatite particle 810. In process 800, sodium azide is the first moiety to bind to polymer constructs. Reacting sodium azide with the hydroxyapatite particle 810 via ethanolic linkers may functionalize the hydroxyapatite particle 810, resulting in functionalized hydroxyapatite (HA) particle 820 with an azide-functionalized exposed surface.

Process 800 may continue by reacting hydroxyapatite particle 820 with a functionalized polymer construct, in order to bind the hydroxyapatite particle 820 with the polymer construct. Because hydroxyapatite particle 820 is functionalized with azide functional groups, the functionalized polymer construct is an alkyne-functionalized polymer construct. In process 800, the alkyne-functionalized polymer construct is an alkyne-functionalized PLA 830.

Reacting hydroxyapatite particle 820 with alkyne-functionalized PLA 830 may be a copper catalyzed click chemistry reaction, with copper (I) and a solvent included in the reaction. In some embodiments, as depicted, hydroxyapatite particle 820 is still embedded in wax 815 when hydroxyapatite particle 820 is reacted with, or bound to, alkyne-functionalized PLA 830. In other embodiments, wax 815 is separated, or removed, from hydroxyapatite particle 820 before reacting the hydroxyapatite particle with the alkyne-functionalized PLA 830. Reacting hydroxyapatite particle 820 with alkyne-functionalized PLA 830 may result in polymer-functionalized hydroxyapatite particle 840. Polymer-functionalized hydroxyapatite particle 840 includes a hydroxyapatite particle bound to a polymer construct, specifically a molecule containing PLA. The hydroxyapatite particle 810 may be bound to alkyne-functionalized PLA 830 using any known mechanisms. For example, the hydroxyl groups on the surface of the hydroxyapatite particle 810 may ring open lactide monomers, grafting PLA from the surface.

It should be noted that, in some embodiments, the compounds described herein can contain one or more chiral centers. These can include racemic mixtures, diastereomers, enantiomers, and mixtures containing one or more stereoisomer. Further, the disclosed compounds can encompass racemic forms of the compounds in addition to individual stereoisomers, as well as mixtures containing any of these.

The synthetic processes discussed herein and their accompanying drawings are not to be construed as limiting. One skilled in the art would recognize that a variety of synthetic reactions may be used that vary in reaction conditions, components, methods, etc. In addition, the reaction conditions can optionally be changed over the course of a process. Further, in some embodiments, processes can be added or omitted while still remaining within the scope of the disclosure, as will be understood by a person of ordinary skill in the art.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A hydroxyapatite particle incorporated into a biodegradable polymer construct, the hydroxyapatite particle having a plurality of functionalities on a surface of the hydroxyapatite particle, the hydroxyapatite particle comprising at least:
 a first functionality concentrated on a first surface of the hydroxyapatite particle, wherein the first functionality includes first moieties to bind to biodegradable polymer constructs, and wherein the first surface is bound to the biodegradable polymer construct through the first functionality; and
 a second functionality concentrated on a second surface of the hydroxyapatite particle, the second surface separate from the first surface, wherein the second functionality includes second moieties.

2. The hydroxyapatite particle of claim 1, wherein the first moieties to bind to the polymer constructs are selected from a group consisting of azide groups and alkyne groups.

3. The hydroxyapatite particle of claim 2, wherein the first moieties are azide groups and the polymer constructs are alkyne-functionalized polymer constructs.

4. The hydroxyapatite particle of claim 2, wherein the first moieties are alkyne groups and the polymer constructs are azide-functionalized polymer constructs.

5. The hydroxyapatite particle of claim 1, wherein the polymer constructs comprise at least one of polylactic acid, polycaprolactone, polyglycolic acid, and poly(lactic-co-glycolic) acid.

6. The hydroxyapatite particle of claim 1, wherein the second moieties are bioactive molecules.

7. The hydroxyapatite particle of claim 6, wherein the bioactive molecules are selected from a group consisting of growth factors, growth factor binding domains derived from proteins, protein domains, peptide sequences, proteins, antibodies, antibodies, cytokines, drugs, deoxyribonucleic acid (DNA), and ribonucleic acid (RNA).

8. An article of manufacture comprising a hydroxyapatite particle incorporated into a biodegradable polymer construct, the hydroxyapatite particle having a plurality of functionalities on a surface of the hydroxyapatite particle, the hydroxyapatite particle comprising at least:
 a first functionality concentrated on a first surface of the hydroxyapatite particle, wherein the first functionality includes first moieties to bind to biodegradable polymer constructs, and wherein the first surface is bound to the biodegradable polymer construct through the first functionality; and
 a second functionality concentrated on a second surface of the hydroxyapatite particle, the second surface separate from the first surface, wherein the second functionality includes second moieties.

9. The article of manufacture of claim 8, wherein the first moieties to bind to the polymer constructs include at least one of azide groups and alkyne groups.

10. The article of manufacture of claim 8, wherein the polymer constructs comprise at least one of polylactic acid, polycaprolactone, polyglycolic acid, and poly(lactic-co-glycolic) acid.

* * * * *